(12) United States Patent
Pilgaonkar et al.

(10) Patent No.: US 8,545,890 B2
(45) Date of Patent: *Oct. 1, 2013

(54) ORALLY DISINTEGRATING TABLETS

(75) Inventors: Pratibha Pilgaonkar, Mumbai (IN); Maharukh Rustomjee, Mumbai (IN); Anilkumar Gandhi, Mumbai (IN); Pradnya M. Bagde, Thane (IN)

(73) Assignee: Rubicon Research Private Limited, Mumbai (IN)

( * ) Notice: Subject to any disclaimer, the term of this patent is extended or adjusted under 35 U.S.C. 154(b) by 303 days.

This patent is subject to a terminal disclaimer.

(21) Appl. No.: 12/270,905

(22) Filed: Nov. 14, 2008

(65) Prior Publication Data

US 2009/0087485 A1    Apr. 2, 2009

Related U.S. Application Data

(63) Continuation-in-part of application No. 12/293,857, filed on Sep. 22, 2008.

(30) Foreign Application Priority Data

Mar. 31, 2006  (IN) ............................ 498/MUM/2006
Mar. 30, 2007  (WO) ................. PCT/IN2007/000138

(51) Int. Cl.
*A61K 9/14* (2006.01)

(52) U.S. Cl.
USPC ............ 424/489; 424/464; 424/493; 424/479

(58) Field of Classification Search
None
See application file for complete search history.

(56) References Cited

U.S. PATENT DOCUMENTS

| | | | |
|---|---|---|---|
| 4,293,539 A | 10/1981 | Ludwig et al. | |
| 4,480,068 A | 10/1984 | Santos et al. | |
| 4,719,181 A | 1/1988 | Schobel et al. | |
| 4,906,478 A | 3/1990 | Valentine et al. | |
| 5,178,878 A | 1/1993 | Wehling et al. | |
| 5,298,261 A | 3/1994 | Pebley et al. | |
| 5,460,823 A | 10/1995 | Jensen et al. | |
| 5,464,632 A | 11/1995 | Cousin et al. | |
| 5,576,014 A | 11/1996 | Mizumoto et al. | |
| 5,958,471 A | 9/1999 | Schwarz et al. | |
| 6,030,645 A | 2/2000 | Tritsch et al. | |
| 6,165,511 A | 12/2000 | Schwarz et al. | |
| 6,328,994 B1 | 12/2001 | Shimizu et al. | |
| 6,610,266 B2 | 8/2003 | Withiam et al. | |
| 6,696,484 B2 | 2/2004 | Liao et al. | |
| 6,699,845 B2 | 3/2004 | Oobae et al. | |
| 6,738,873 B2 | 5/2004 | Saltz | |
| 6,740,339 B1 | 5/2004 | Ohkouchi et al. | |
| 6,872,405 B2 | 3/2005 | Takaishi et al. | |
| 6,998,481 B2 | 2/2006 | Erdmann et al. | |
| 6,998,482 B2 | 2/2006 | Erdmann et al. | |
| 7,070,805 B2 | 7/2006 | Shimizu et al. | |
| 2001/0014340 A1 | 8/2001 | Ohta et al. | |
| 2002/0076437 A1 | 6/2002 | Kothari et al. | |
| 2003/0203036 A1 | 10/2003 | Gordon et al. | |
| 2004/0071772 A1 | 4/2004 | Narita et al. | |
| 2005/0054559 A1 | 3/2005 | Gallop et al. | |
| 2005/0106240 A1 | 5/2005 | Tanaka et al. | |
| 2005/0147666 A1 | 7/2005 | Ohta et al. | |
| 2006/0134199 A1 | 6/2006 | Suga et al. | |
| 2006/0163534 A1 | 7/2006 | Sugimoto et al. | |
| 2006/0177499 A1 | 8/2006 | Besse | |
| 2006/0276473 A1 * | 12/2006 | Bostion et al. | ................ 514/241 |
| 2007/0048374 A1 | 3/2007 | Shah et al. | |
| 2007/0077301 A1 | 4/2007 | Meyer et al. | |
| 2007/0104785 A1 | 5/2007 | Navale et al. | |
| 2007/0110808 A1 | 5/2007 | Bhattacharya et al. | |
| 2007/0196475 A1 | 8/2007 | Withiam et al. | |
| 2007/0243248 A1 | 10/2007 | Cherukuri | |
| 2007/0269510 A1 | 11/2007 | Nimbalkar et al. | |
| 2007/0275058 A1 | 11/2007 | Tanaka et al. | |
| 2007/0275059 A1 | 11/2007 | Kothari et al. | |
| 2007/0298107 A1 | 12/2007 | Aluri et al. | |

FOREIGN PATENT DOCUMENTS

| | | |
|---|---|---|
| EP | 1 145 711 | 10/2001 |
| EP | 1 488 811 | 12/2004 |
| EP | 1 681 048 | 7/2006 |
| EP | 1 862 184 | 12/2007 |
| JP | 11302157 | 11/1999 |
| JP | 2000 086537 | 3/2000 |
| JP | 2000-086537 | 3/2000 |
| JP | 2006052167 | 2/2006 |
| WO | WO 91/04757 | 4/1991 |
| WO | WO 97/36879 | 10/1997 |
| WO | WO 00/57857 | 10/2000 |
| WO | WO0202128 A2 | 1/2002 |
| WO | WO 03/045844 | 6/2003 |
| WO | WO 03/051338 | 6/2003 |
| WO | WO03045844 A1 | 6/2003 |
| WO | WO03051338 A1 | 6/2003 |
| WO | WO 2004 082664 | 9/2004 |
| WO | WO 2004 096214 | 11/2004 |
| WO | WO 2006/100875 | 9/2006 |
| WO | WO 2007 097333 | 8/2007 |
| WO | WO 2007 113856 | 10/2007 |
| WO | WO 2008/079343 | 7/2008 |

* cited by examiner

*Primary Examiner* — Hasan Ahmed

(74) *Attorney, Agent, or Firm* — Hoffmann & Baron, LLP

(57) ABSTRACT

The present invention describes a directly compressible composite excipient prepared by coating calcium silicate with a carbohydrate. The present invention further describes the incorporation of the composite excipient into a tablet formulation. The orally disintegrating tablets are of optimal mechanical strength and disintegrate within 60 seconds in the oral cavity.

9 Claims, 6 Drawing Sheets

SEM of the Composite Excipient

SEM of Composite Excipient

SEM of Calcium Silicate

SEM of Mannitol

SEM of Physical mix of Mannitol and Calcium Silicate

ORALLY DISINTEGRATING TABLETS

CROSS REFERENCE TO RELATED APPLICATIONS

This application is a continuation-in-part application of U.S. patent application Ser. No. 12/293,857, filed Sep. 26, 2008, which is a national stage application of PCT/IN2007/000138, filed Mar. 30, 2007, which claims the benefit of Indian Application No. 498/MUM/2006, filed Mar. 31, 2006.

BACKGROUND OF INVENTION

The present invention provides a tablet with optimal mechanical strength, which when placed in the oral cavity rapidly dissolves or disintegrates without water, preferably within about 60 seconds.

More particularly, the present invention relates to composite excipients produced by substantially completely coating calcium silicate with a carbohydrate, and the use of these composite excipients in orally disintegrating tablets.

Design of an orally disintegrating tablet requires a significant amount of research work in order to develop a process that maintains enough porosity inside the compressed tablets for fast dissolving or fast melting while maintaining the mechanical strength of the tablet. Orally disintegrating dosage forms are known in the art and some of the most commonly used techniques are incorporated herein by reference Current technologies involved in many patents as well as existing commercial fast-dissolving tablets utilize complicated processing techniques such as freeze-drying, molding and sublimation or use of specialized excipients such as effervescent couple, highly micronized agents or the likes.

Freeze drying is one common process for producing many commercial fast dissolving tablets wherein a cake or wafer is prepared by freeze drying a solution or suspension of the medicament and suitable excipients in water or other solvents. Such systems dissolve very rapidly on the tongue, due to their high affinity for moisture and a very high porosity. U.S. Pat. No. 5,298,261 discloses freeze-drying a slurry or paste comprising an active ingredient and excipients placed in blister packets. PCT application WO 97/36879 discloses vacuum drying, at room temperature or a slightly elevated temperature, of a suspension including the active drug, a sugar alcohol, PEG 6000, talc, sweeteners and flavors, in preformed blisters. However, the freeze-drying process suffers from several disadvantages. The primary disadvantage is that solutions employed for freeze-drying are aqueous and, therefore, not suited for water sensitive medicaments. Freeze-drying is also limited to low dose actives. The process itself is typically laborious, costly and time-consuming. Finally, the resultant dosage forms, in addition to being hygroscopic, tend to be very soft, and therefore require special moisture-resistant and impact-resistant packaging and careful handling.

U.S. Pat. No. 5,464,632 claims the use of high levels of disintegrants, such as 16% starch 1500 and 13.3% crospovidone, for a disintegration time of 35 seconds to 45 seconds. However, such tablets have a chalky or dry feel when placed in the mouth.

U.S. Pat. No. 5,178,878 discloses a rapidly dissolving oral formulation that requires an extragranular microparticulate active in conjunction with an effervescent agent incorporated into a tableted matrix in order to achieve rapid oral disintegration. Many fast-dissolving tablets are also formulated by the inclusion of effervescent compounds. U.S. Pat. No. 5,178,878 and WO 91/04757 disclose the addition of an effervescent couple (such as sodium bicarbonate and citric acid) to a tablet. Exposure of such tablet to moisture results in contact and chemical reaction between the effervescent couple which leads to gas production and tablet disintegration. However, tablets which include effervescent pairs are highly sensitive to moisture and require a specific, very costly plant including special handling equipment, controlled-humidity environments, as well as special moisture resistant packaging. Such preparations have an unpleasant mouth feel.

Another orally disintegrating technique is spray drying technology as explained in U.S. Pat. Nos. 5,958,471 and 6,165,511, which includes preparing an aqueous solution of more than 80% of one or more non-hygroscopic polyols, and spraying the resulting mixture into an air stream. The resulting composition of the spray-drying process contains a filamentous structure. Similarly PCT application WO 03/051338A1 relates to a method for producing a directly compressible and highly compactible composition by co-spray drying of mannitol and sorbitol solution resulting in nonfilamentous microstructure. Both these patents describe use of highly concentrated aqueous solutions, which are to be maintained and sprayed at high temperature, thus demanding special equipment.

Another approach to develop orally disintegrating dosage form involves optimal selection of excipients which would result in desired disintegration time. These are typically compressed dosage forms. EP 1145711 describes the preparation of flash-melt dosage forms that disintegrate in the mouth in less than 25 second. They consist of granules composed of a superdisintegrant (4-8%), a dispersing agent such as calcium silicate (20-70%), a distributing agent selected from amorphous silica, fumed silica, diatomaceous earth, talc, kaolin, magnesium aluminum trisilicate, and a binder (10 to 50% by weight). Although a larger amount of binder may produce stronger tablets, the disintegration times tend to increase. To counter this, a large amount of dispersing and distributing agent is included in the formulation which increases the weight of the tablet. This may increase the cost of the formulation.

PCT application WO 03/045844A1 relates to synthetic calcium metasilicate, which when incorporated in a solid product, significantly increases the disintegration rate of the formed product when contacted by a substantially aqueous environment. The reduction in disintegration time with calcium silicate is more pronounced with immediate release tablets, as tablets prepared with calcium silicate have lower porosity. Further, the use of calcium silicate with conventional equipments leads to discoloration of the final dosage form due to interaction of calcium silicate with some metals, as well as reaction with many active pharmaceutical agents (hereinafter the "API".) Calcium silicate, due to its hydrophobic and static nature, results in blends with very poor flow properties causing weight and content variation during compression into tablets. Further, it also imparts a chalky taste to the dosage form.

In general, there are numerous other examples of specific formulations that utilize one or more of the techniques or mechanisms discussed above. Majority of these techniques possess one or more of the above enumerated disadvantages to some extent such as tedious and complex method of manufacturing, special packaging and storage requirements, high cost, limitation on drug load etc. Thus, there continues to be a need for a formulation that mitigates or eliminates these disadvantages. The desired features of such dosage form include quick disintegrability in an oral cavity, a pleasant mouth feel and optimal mechanical strength even in storage under a humidifying conditions.

It was surprisingly found that composite excipients made by co-processing of at least one water soluble excipient and at least one water insoluble excipient such as calcium silicate, leads to a formulation that rapidly disintegrates or dissolves on in the mouth. More specifically, it has been discovered that a composite excipient formed by substantially completely coating the calcium silicate in a carbohydrate, the calcium silicate is prevented from reacting with the API or processing equipment, and further exhibits greatly improved flow properties.

Tablets made with this improved composite excipient exhibit low friability, low ejection forces and hardness sufficient to be processed in high speed tableting machines and shipped in low cost packages, while retaining rapid disintegration or dissolution properties. The tablets have a pleasant mouth feel and good mechanical strength such that they do not require special handling or packaging conditions.

SUMMARY OF INVENTION

In one illustrative embodiment of the present invention there is provided a directly compressible composite excipient for orally disintegrating tablets comprising at least one water-soluble excipient and calcium silicate prepared by co-processing.

According to another aspect of the invention is provided an orally disintegrating tablet formulation having optimal mechanical strength comprising a. at least one pharmaceutically active ingredient or a nutraceutical agent b. composite excipients produced by co-processing of mannitol and calcium silicate. c. at least one other excipient such that the tablet has optimal mechanical strength and a disintegration time of about 60 sec in the oral cavity.

In one illustrative aspect of the present invention there is provided a composite excipient comprising calcium silicate particles substantially completely covered by at least one carbohydrate.

In another illustrative aspect of the present invention there is provided a composite excipient comprising calcium silicate particles substantially completely covered by mannitol.

In still another illustrative aspect of the present invention there is provided a method of making a composite excipient, the method comprising adding at least one carbohydrate to water; heating the solution to a temperature at which the at least one carbohydrate is substantially dissolved to form a solution; adding calcium silicate with stirring to the solution to form a slurry; and drying the slurry in a heated air stream to form calcium silicate that is substantially completely covered in the carbohydrate.

In yet another illustrative aspect of the present invention there is provided an orally disintegrating tablet comprising at least one pharmaceutically active ingredient and a composite excipient comprising calcium silicate substantially completely covered with at least one carbohydrate.

DETAILED DESCRIPTION

Figure 1:
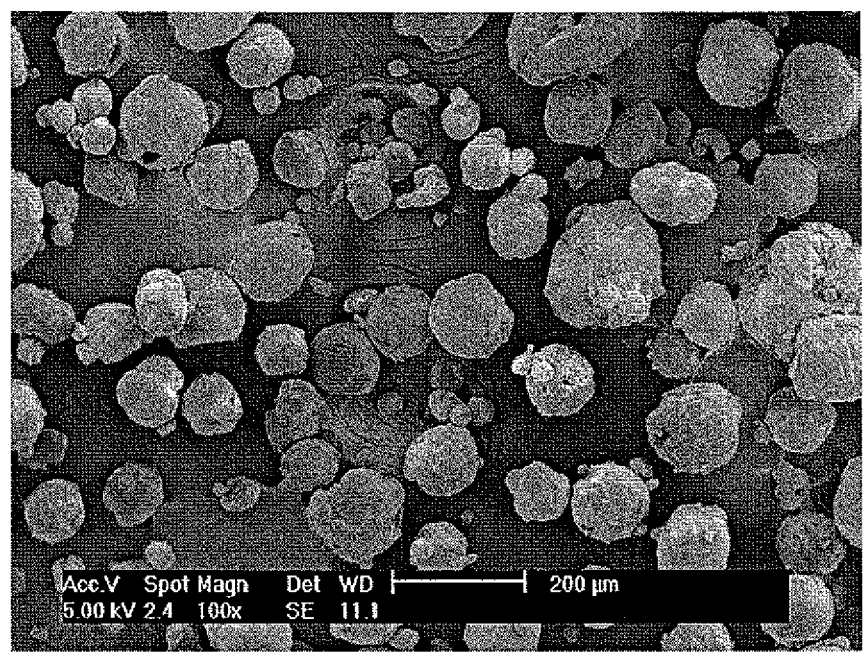
FIG. 1 is an illustration of a SEM micrograph of the composite excipient of the present invention according to Example 19.

Solid pharmaceutical dosage forms that rapidly dissolve or disintegrate in a glass of water or in the gastrointestinal tract have been known in the art for many years. The obvious advantages of the convenience of carrying dosage forms that will dissolve or effervesce in water to release medicaments are well known. Rapid disintegration technology is among the most exciting recent developments in the pharmaceutical industry. Orally Disintegrating Tablets (hereinafter ODT) are tablets that disintegrate/dissolve in the mouth rapidly without administering extra water. These dosage forms provide the convenience of a tablet formulation while allowing the ease of swallowing provided by a liquid formulation. Such dosage forms due to their ease of administration and pleasant mouth feel, may encourage patients especially children, the elderly and schizophrenic patients who have difficulty in swallowing conventional tablets to adhere to daily medication regimens and also allow the luxury of much more accurate dosing than oral liquids. Yet another situation where such tablets would be useful is where water may not be readily available to assist in swallowing the tablet in specific conditions.

The term 'Co-processed excipient' as used here refers to a composite excipient in which at least two excipients are present in close proximity to each other. In one of the embodiments such composite excipient may have one excipient incorporated in the particle structure of the other.

The term 'porosity' as used here is a measure of void spaces within the material and is measured as a fraction (between 0 to 1) or as a percentage value (between 0 to 100%). Porosity is the ratio of void space to bulk volume. It can be determined using the following formula:

$$\text{Porosity} = (\text{Bulk volume} - \text{True volume})/\text{Bulk volume}$$

The term 'wicking time' as used here provides time (seconds) taken for water to wick into the tablet and completely wet the tablet core. The wicking time test is used to evaluate the performance of orally disintegrating tablets. The wicking time determination is carried out in a petri plate (~10 cm in diameter). The plate is layered with tissue papers of ~0.25 mm thick. The tissue paper is wetted with 10 ml water (preferably colored using a water soluble dye) and allowed to soak for 30 sec. A tablet is then placed on the wetted tissue paper and the time taken by water to reach the surface of tablet and completely wet it is recorded as the 'wicking time'. The test may be appropriately modified for tablets having weight of more than 200 mg.

The term 'mouth dissolution time' as used here provides time (seconds) taken for tablet to completely dissolve in the mouth determined in and by human volunteers.

The term 'lag time' as used here provides time (seconds) taken for tablet to soften and start disintegrating after being placed on the tongue determined in and by human volunteers.

The term 'in vitro disintegration time' as used here refer to the time taken for complete disintegration of the tablet as determined using the USP disintegration apparatus.

Composite excipients are excipients formed from at least two separate excipients. In the present invention, the composite excipient is formed by coating calcium silicate with at least one carbohydrate. In an illustrative embodiment the carbohydrate is mannitol.

The preferred carbohydrates include water soluble carbohydrates. The water soluble carbohydrates can be a monosaccharide, disaccharide, oligosaccharide, polysaccharide or mixtures thereof. Examples include but are not limited to monosaccharides such as glyceraldehyde, erythrose, threose, ribose, arabinose, xylose, allose, altrose, glucose, mannose, fructose, gulose, idose, galactose, talose and sorbitol; disaccharides such as maltose, lactose, cellobiose, sucrose, mannitol, trehalose and mixtures thereof; oligosaccharides such as raffinose, stachyose, dextrates and mixtures thereof; or polysaccharides such as maltodextrins, starch, glycogen, cellulose, chitin, callose, galactomannan, xylan, laminarin and mixtures thereof. The saccharide is preferably at least one selected from mannitol, lactose, saccharose, trehalose, xylitol, erythritol and mixtures thereof. In an illustrative embodiment, the saccharide is mannitol. These water soluble excipients can be employed alone or in combination.

The preferred calcium silicate is a calcium metasilicate. An illustrative embodiment of a suitable calcium silicate is marketed by Huber as RXCIPIENT® FM1000, having an aspect ratio of about 1:1 to about 2.5:1 and an oil absorption of from about 20 ml/100 g to 220 ml/100 g. It is a unique physical form of Calcium Silicate, which reduces the disintegration time of a dosage form. This calcium silicate is the subject of U.S. Pat. No. 6,610,266, incorporated herein by reference. Another illustrative embodiment of suitable calcium silicate is a porous calcium silicate with a density of less than 0.2 g/cc marketed by Preeti Industries.

The carbohydrate and calcium silicate may be present in the composite excipients in the ratio of 1:50 to 50:1; preferably 1:30 to 30:1 and more preferably 1:20 to 20:1. In an illustrative embodiment, the composite excipient of the present invention comprises from about 50% to about 95% carbohydrate, and from about 5% to about 50% calcium silicate. In a non-limiting, illustrative embodiment of the present invention, the composite excipient comprises about 75% mannitol and about 25% calcium silicate.

Any process that ensures the substantially complete coating of the calcium silicate with the carbohydrate can be employed. While a complete covering is ideal, in practice the coating will tend to include imperfections, and is therefore referred to as 'substantially complete.' Suitable processes that ensure substantially complete coverage of the calcium silicate include spray drying and fluidized bed processing. The preferred method for preparing the composite excipient of the present invention is spray drying.

Spray drying is an industrial process involving particle formation and drying. It is highly suited for the continuous production of dry solids in either powder, granulate or agglomerate form from liquid feedstock such as solutions, emulsions and pumpable suspensions. Spray drying is an ideal process where the end-product must comply with precise quality standards regarding particle size distribution, residual moisture content, bulk density, and particle shape. Spray drying involves the atomization of a liquid feedstock into a spray of droplets that are contacted with hot air in a drying chamber. The sprays are produced by either rotary (wheel), nozzle, or ultrasonic atomizers. Evaporation of moisture from the droplets as the dry particles are formed proceeds under controlled temperature and airflow conditions. The dry product is discharged continuously from the drying chamber. Operating conditions and dryer design are selected according to the drying characteristics of the desired product, as is known in the art.

There are a number of variables in the spray drying process, including feed composition, feed viscosity, density, feed spray rate, inlet temperature, outlet temperature, temperature difference, atomization pressure, vacuum and residence time, which can be varied in order to achieve the desired product.

An illustrative process employed to produce the present invention composite excipient comprises dissolving the carbohydrate in a suitable aqueous solvent, typically water, and then adding the calcium silicate to form a slurry. The slurry may be preheated under stirring before being fed into the spray drying chamber, and may be sprayed with a single fluid nozzle or a two-fluid nozzle. Alternatively, the slurry may be sprayed using a rotating disk. The drying of the particles could be achieved using any of the methods such as co-current flow, counter current flow or mixed flow. The total solid content of the feed could vary from about 2-75%, preferably from 5-60% and more preferably from 10-50%. In a non-limiting, illustrative embodiment, the solid content is about 20% to about 40%.

The calcium silicate/carbohydrate composite excipients produced by the instant invention have improved properties. The moisture content of the composite excipient, as determined using loss on drying, is preferably less than 2%. The porosity of the composite excipient plays a crucial role in the performance of the orally disintegrating tablet. In order to have disintegration time of less than 60 seconds, the porosity of the tablet should be at least about 50%. Another parameter which determines the wicking time, disintegration time in oral cavity and lag time is the particle size distribution of the composite. This parameter also determines the flow of the blend ready for compression into tablets. It is desirable that not less than 40% of particles are less than 150 microns.

In an illustrative embodiment, the mannitol is dissolved in deionized water in a mixing chamber, and calcium silicate is then added to the solution to form a slurry. The slurry was mixed at an elevated temperature using an agitator to keep solid suspended in the solution to form a uniform slurry. The preferred temperature is high enough to ensure that the mannitol is substantially dissolved, and that the mannitol properly coats the calcium silicate, typically at least 30° C., for example 40° C. to 60° C. The slurry mixture was then spray dried through a rotary nozzle. Composite excipients formed according to this process, described in more detail in Example 19, can be seen in the SEM micrographs illustrated in FIGS. 1 and 2. The SEM show the unique morphology of the composite excipient obtained according to this invention wherein calcium silicate particles are thought to be assembled together in the core of the particle and the particle is coated by mannitol. The average particle size of this composite is preferable at least about 50 micrometers, typically about 90 micrometers, while the calcium silicate starting material particle size is less than 7 um, which may indicate some type of aggregation of the particles. As such the composite reduces the calcium silicate particle contact with the API, other excipients or tableting equipment, thereby providing improved processing and tablets.

Figure 3:
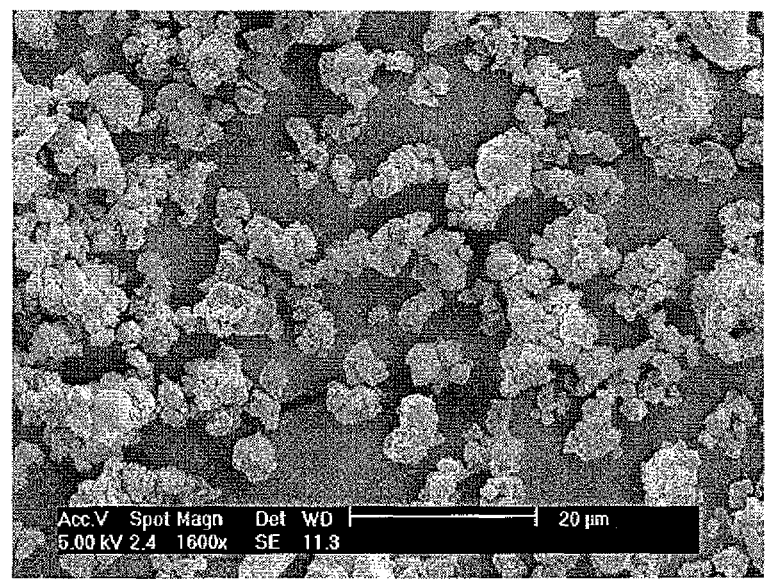
FIG. 3 is an illustration of a SEM micrograph of calcium silicate.
Figure 4:
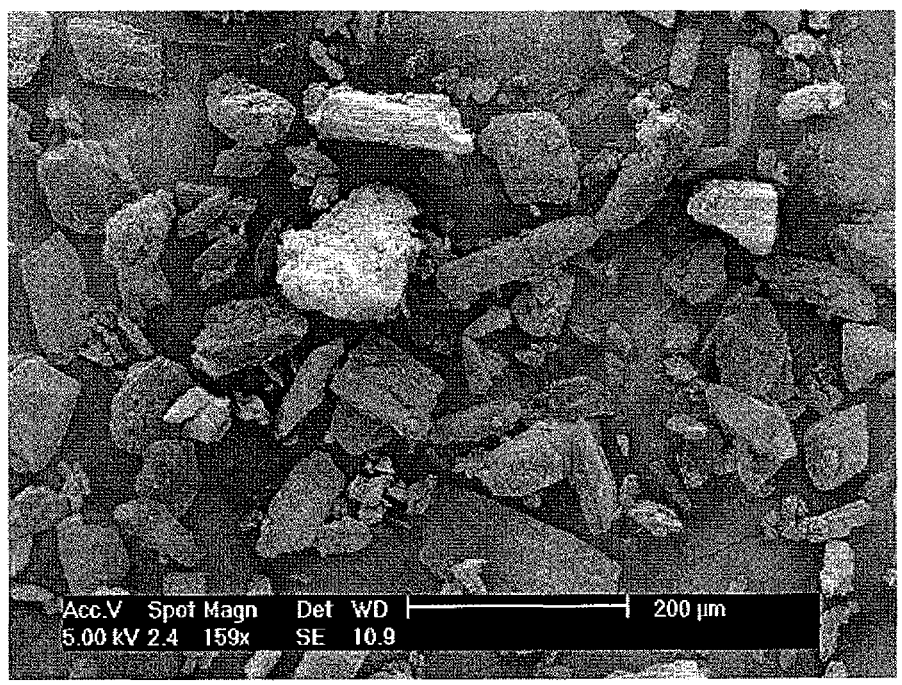
FIG. 4 is an illustration of a SEM micrograph of mannitol.

The SEM micrographs of the composite excipient of the present invention are contrasted to SEM micrographs of the individual components. SEM micrographs illustrate that calcium silicate is a very fine material (see FIG. 3), whereas mannitol exhibits large irregular crystals (see FIG. 4.) A physical mixture of mannitol and calcium silicate was prepared according to Example 24. A SEM micrograph of the physical mix (see FIG. 5) suggests that during physical mixing the small particles of calcium silicate coats the mannitol particle as a result of which none of the properties/limitations of calcium silicate are masked, but the properties of mannitol are partially masked. Thus the resulting product has poor flow, poor compressibility and is blackened during processing.

Active Pharmaceutical Ingredients. As used herein, the term API refers to one or more compounds that have some pharmacological property. There is no limitation to the API that can be used with the present invention. API can be included in the tablet compositions as is or coated with a suitable taste masking agent. The compositions of the invention contain at least one suitable pharmaceutical active ingredient or nutraceutical active ingredient. Examples of API that can be used include, but are not limited to gastrointestinal function conditioning agents anti-inflammatory agents, including, but not limited to aceclofenac, diclofenac, ibuprofen flubiprofen, piroxicam, sulindac, and celecoxib; analgesics, including, but not limited to acetaminophen, fentanyl, tramadol and aspirin; agents for erectile dysfunction therapy, including, but not limited to sildenafil and apomorphine; anti-migraines, including, but not limited to sumatriptan, rizatriptan, zolmitriptan, naratriptan and ergotamin; antihistaminic agents, including, but not limited to loratadine, fexofenadine, pseudoephedrine and cetirizine; cardiovascular agents, including, but not limited to nitroglycerine and isosorbide dinitrate; diuretics, including, but not limited to furocemide and spironolactone; anti-hypertensive agents, including, but not limited to propranolol, amlodipine, felodipine, nifedipine, captoprile, ramiprile, atenolol, and diltiazem; anti-hypolipidemic agents, including, but not limited to simvistatin, atrovastatin, and pravastatin; anti-ulcer agents, including, but not limited to cimietidine, ranitidine, famotidine, omeprazole, esomeprazole, rabeprazole and lansoprazol; anti emetics, including, but not limited to meclizine hydrochloride, ondansetron, granisetron, ramosetron, and tropisetron; anti-coagulants such as ticlopidine hydrochloride, dicumarol, or warfarin potassium; antiepileptics such as phenytoin sodium, and lamotrigine, antiasthmatic agents, including, but not limited to aminophylline, theophylline, terbuttaline, fenoterol, formoterol, and ketotifen; brain metabolism altering drugs such as meclofenoxate hydrochloride; minor tranquilizers such as oxazolam, diazepam, clonazepam, clotiazepam, medazepam, temazepam, fludiazepam, nitrazepam, alprazolam, lorazepam or chlordiazepoxide; anti-depressants, including, but not limited to fluoxetine, mirtazepine, escitalopram and sertraline; drugs for treatment of parkinson's disease or restless leg syndrome such as ropinirole hydrochloride; drug for alzheimer's disease such as memantine; drugs for schizophrenia such as risperidone, olanzepine and aripiprazole; oral antibacterial and antifungal agents such as penicillin, ampicillin, amoxicillin, cephalexin, erythromycin ethylsuccinate, acampicillin hydrochloride, minocycline hydrochloride, chloramphenicol, tetracycline, erythromycin, fluconazole, itraconazole, ketoconazole, miconazole or terbinafine; synthetic antibacterial agents such as nalidixic acid, piromidic acid, pipemidic acid trihydrate, enoxacin, cinoxacin, ofloxacin, norfloxacin, ciprofloxacin hydrochloride, or sulfamethoxazole trimethoprim; antispasmodics such as propantheline bromide, atropine sulfate, oxapium bromide, timepidium bromide, antitussive, anti-asthmatic agents; muscle relaxants such as chlorphenesin carbamate, tolperisone hydrochloride, eperisone hydrochloride, tizanidine hydrochloride, mephenesin, chlorozoxazone, phenprobamate, methocarbamol, chlormezanone, pridinol mesylate, afloqualone, baclofen, or dantrolene sodium; oral antidiabetic agents such as glibenclamide, tolbutamide, or glymidine sodium; circulatory agents such as ubidecarenone or ATP-2Na; iron preparations such as ferrous sulfate or dried ferrous sulfate; vitamins such as vitamin B1, vitamin B2, vitamin B6, vitamin B 12, vitamin C, vitamin A, vitamin D, vitamin B, vitamin K or folic acid; pollakiuria remedies such as flavoxate hydrochloride, oxybutynin hydrochloride, terodiline hydrochloride, or 4-diethylamino-1,1-dimethyl-2-butynyl (I)-a-cyclohexyl-oc-phenylglycolate hydrochloride; angiotensin-converting enzyme inhibitors such as enalapril maleate, antiviral agents such as trisodium phosphonoformate, didanosine, dideoxycytidine, azido-deoxythymidine, dide-hydro-deoxythymidine, adefovir dipivoxil, abacavir, amprenavir, delavirdine, efavirenz, indinavir, lamivudine, nelfinavir, nevirapine, ritonavir, saquinavir or stavudine, as well as mixtures thereof.

Examples of nutraceutical ingredients include, but are not limited to any ingredient that is thought to have a beneficial effect on human health. Such ingredients include coenzyme Q-IO, chondroitoin, echinacea, ephedra, glucosamine, garlic, ginkgo biloba, ginseng, grape seed extract, guarana, hawthorn, herbs, kava, kola nut, lutein, St. John's wort, vinpocetine, and yohimbe, as well as mixtures thereof.

The API may be present in any form such as its normal form, taste masked form, enteric or controlled release form. The taste masking can be carried out by any of the processes known in the art, not limiting to complexation with cyclodextrins, ion exchange resins or any other suitable agents. Taste masking can also be achieved by coating with water soluble or insoluble polymers or polymers having pH dependent solubility or waxes. Both the enteric release and controlled release may demand for coating of active ingredient or its granules with suitable retardants or polymers.

The API may be incorporated in the formulation in the form of powder or granules, or as a taste masked form of powder form, granules, pellets, beads or any other form.

The tablets of the invention may include in addition to the composite and an active ingredient, one or more binders, disintegrants, superdisintegrants, diluents, salivating agents, surfactants, flavors, sweeteners colorants, diluents, souring agents, suitable taste masking agents, viscosity builders, glidants or lubricants, solubilizers, and stabilizers.

The compositions of the invention also include at least one super disintegrant selected from but not limited to natural, modified or pregelatinized starch, crospovidone, croscarmellose sodium, sodium starch glycolate, low-substituted hydroxypropyl cellulose as well as effervescent disintegrating systems. Preferred disintegrants in the invention include crospovidone and natural, modified or pregelatinized starch. The amount of superdisintegrant employed in the composition is about 2-50% by weight of the said dosage form.

Examples of suitable binders include starch, pregelatinized starch, cellulose derivatives, such as hydroxypropylmethyl cellulose (HPMC), hydroxypropyl cellulose (HPC) and carboxymethyl cellulose (CMC) and their salts. Examples of suitable diluents include starch, dicalcium phosphate, microcrystalline cellulose and the like.

Examples of the lubricant include but not limited to magnesium stearate, calcium stearate, stearic acid, talc, and sodium fumarate stearate. The compositions of the invention may also include a glidant selected from colloidal silica, silica gel, precipitated silica, or combinations thereof. The said compositions may also include salivating agents such as but not limited to micronised polyethylene glycol preferably of molecular weight 4000, sodium chloride or precipitated micronised silica to improve the disintegration properties of the said compositions.

In addition to above excipients, the compositions of the invention also include at least one sweetening agent selected from aspartame, stevia extract, glycyrrhiza, saccharine, saccharine sodium, acesulfame, sucralose and dipotassium glycyrrhizinate; one or more flavors e.g., mint flavor, orange flavor, lemon flavors, strawberry aroma, vanilla flavor, raspberry aroma, cherry flavor, magnasweet 135, key lime flavor, grape flavor trusil art 511815, fruit extracts and colours or dyes. There is no limitation on color or flavor that is useful in the present invention, and these characteristics will likely be chosen based on the age of the patient consuming the solid dosage form.

The term "solid dosage form" may refer to tablets or granules. However the most preferred dosage form is tablet. The term tablet is construed to include a compacted or compressed powder composition obtained by compressing or otherwise forming the composition to form a solid having a defined shape. Tablets in accordance with the invention may be manufactured using conventional techniques of common tableting methods known in the art such as direct compression, wet granulation, dry granulation and extrusion/melt granulation. The preferred process is direct compression which involves compression of drug-excipient blend after mixing them for a definite time period.

The tablet may vary in shape such as oval, triangle, almond, peanut, parallelogram, round, pentagonal, hexagonal, and trapezoidal. The preferred shapes are round, oval and parallelogram forms.

The performance of the orally disintegrating tablets formulated with the composite excipient of the present invention can be evaluated using a number of parameters namely wicking time, disintegration time in oral cavity, in vitro disintegration time, lag time etc. As per various embodiments of the present invention, both the wicking time and disintegration time in oral cavity are less than 60 seconds and the lag time is less than 10 seconds.

While the present invention has been described in terms of its specific embodiments, certain modifications and equivalents will be apparent to those skilled in the art and are intended to be included within the scope of the present invention. The details of the invention, its objects and advantages are explained hereunder in greater detail in relation to non-limiting exemplary illustrations.

EXAMPLES

Example 1

Co-Processing of Mannitol and Calcium Silicate by Spray Drying 180 gms of mannitol was dissolved in water at about 80° C. temperature. In this solution 20 gms of calcium silicate was added and stirred to get a uniform mass. The mass was sprayed in the spray dryer under following conditions:

| Inlet Temperature | 180-200° C. |
|---|---|
| Outlet Temperature | 80-120° C. |
| Nozzle Diameter | 1 mm |
| Feed Rate | 150-200 ml/hr |
| Atomisation pressure | 0.7-1.2 Kg/cm2 |

The composites obtained were free flowing with bulk density in the range of 0.3-0.5 gm/cc and having about 75% of particles below 150 microns.

Spray Drying of Mannitol:

Mannitol alone was also spray dried under above mentioned conditions.

Example 2

Co-Processing of Mannitol, Sorbitol and Calcium Silicate by Spray Drying 160 gms of mannitol and 20 gms of sorbitol were dissolved in water at 70-75° C. temperature. In this solution 20 gms of calcium silicate was added and stirred to get a uniform mass. The mass was sprayed in the spray dryer under following conditions:

| Inlet Temperature | 180-200° C. |
|---|---|
| Outlet Temperature | 70-100° C. |
| Nozzle Diameter | 1 mm |
| Feed Rate | 150-200 ml/hr |
| Atomisation pressure | 3-4 Kg/cm$^2$ |

The composites obtained were free flowing with bulk density of 0.4-0.5 gm/cc

Example 3

Co-Processing of Mannitol, Microcrystalline Cellulose and Calcium Silicate by Spray Drying 160 gms of mannitol was dissolved in water at about 70° C. temperature. In this solution 20 gms of calcium silicate and 20 gms of microcrystalline cellulose were added and stirred to get a uniform mass. The mass was sprayed in the spray dryer under same conditions as given in example 2. The composites obtained were free flowing with bulk density of 0.4 gm/cc.

Example 4

Co-Processing of Mannitol and Calcium Silicate by Spray Drying 240 g Mannitol was dissolved in 4.0 liter water at room temperature. In this solution 560 g of calcium silicate was added and stirred to get a homogeneous mass. The mass was sprayed in the spray dryer under following conditions:

| Inlet Temperature | 200-220° C. |
|---|---|
| Outlet Temperature | 80-120° C. |
| Nozzle Diameter | 2 mm |
| Feed Rate | 70-90 ml/hr |
| Atomisation pressure | 0.2 Kg/cm$^2$ |

The composites obtained were free flowing with bulk density of 0.55-0.65 gm/cc and moisture content of less than 1.0% determined by loss on drying. About 90% of the particles were of size less than 150 microns and the composite had a desirable porosity of 63%.

Example 5

Co-Processing of Mannitol and Calcium Silicate by Spray Drying 600.0 g Mannitol was dissolved in 3.0 liter water at room temperature. In this solution 600.0 g of calcium silicate was added and stirred to get a uniform mass. The mass was sprayed in the spray dryer under following conditions:

| Inlet Temperature | 200-205° C. |
|---|---|
| Outlet Temperature | 105-125° C. |
| Nozzle Diameter | 2 mm |
| Feed Rate | 70-90 ml/hr |
| Atomisation pressure | 0.2 Kg/cm$^2$ |

The composites obtained had moisture content of less than 1%, porosity of 65% and were free flowing with bulk density of 0.6-0.8 gm/cc

Example 6

Co-Processing of Mannitol, Calcium Silicate and Polyethylene Glycol by Spray Drying 340.0 g Mannitol and 20.0 g of Polyethylene glycol were dissolved in 2.0 liter water at room temperature. In this solution 40.0 gms of calcium silicate was added and stirred to get a uniform mass. The mass was sprayed in the spray dryer under following conditions:

| | |
|---|---|
| Inlet Temperature | 200-205° C. |
| Outlet Temperature | 105-125° C. |
| Nozzle Diameter | 2 mm |
| Feed Rate | 70-90 ml/hr |
| Atomisation pressure | 0.2 Kg/cm$^2$ |

The composites obtained were free flowing with bulk density of 0.5-0.7 gm/cc and moisture content 0.5%. The porosity of the composite was 61%.

Example 7

Co-Processing of Mannitol and Calcium Silicate by Spray Drying Using a Rotary Disc 900.0 g Mannitol was dissolved in 5.0 liter water at room temperature. In this solution 100.0 gms of calcium silicate was added and stirred to get a uniform mass. The mass was sprayed in the spray dryer under following conditions:

| | |
|---|---|
| Inlet Temperature | 200-205° C. |
| Outlet Temperature | 85-95° C. |
| Nozzle Diameter | 2 mm |
| Rotary Disk Radius | 6 cm |
| Rotary Disk Speed | 24000 rpm |
| Feed Rate | 70-90 ml/hr |

The composites obtained possessed bulk density of 0.45-0.55 gm/cc and had a good flow. The moisture content was about 0.6% with about 95% of particles below 150 microns.

Example 8

Tablet Formulation Using Composite of Mannitol and Calcium Silicate and Spray Dried Mannitol

TABLE 1

Compositions of orally disintegrating tablets using composites and spray dried mannitol

| Ingredients | A mg/tablet | B mg/tablet |
|---|---|---|
| Spray dried mannitol of example 1 | 45.0 | — |
| Co-processed composite of example 1 | — | 50.0 |
| Starch | 23.0 | 23.0 |
| Microcrystalline cellulose | 10.0 | 10.0 |
| Croscarmellose sodium | 3.5 | 3.5 |
| Calcium silicate | 10.0 | 5.0 |
| Aspartame | 1.5 | 1.5 |
| Colloidal silicon dioxide | 0.8 | 0.8 |
| Flavor | 0.5 | 0.5 |
| Polyethylene Glycol | 5.0 | 5.0 |
| Flavor | 0.2 | 0.2 |
| Sodium stearyl fumarate | 0.5 | 0.5 |
| Total | 100.0 | 100.0 |

All excipients except lubricant were blended in a blender to get a uniform mass. The mass was lubricated and compressed into tablets having following parameters:

TABLE 2

| | A | B |
|---|---|---|
| Hardness (N) | 10-20 | 10-20 |
| Friability (%) | 0.85 | 1.0 |
| In vitro disintegration time (sec) | 15-20 | 5-10 |
| Disintegration time in oral cavity (sec) | 40-50 | 25-40 |

Robust tablets were obtained with low friability and desired disintegration time.

Example 9

Tablet Formulation Using Composite of Mannitol, Microcrystalline Cellulose and Calcium Silicate

TABLE 3

Compositions of orally disintegrating tablets using composite of example 3

| Ingredients | mg/tablet |
|---|---|
| Coprocessed composite of example 4-3 | 55.0 |
| Starch | 23.0 |
| Microcrystalline cellulose | 5.0 |
| Croscarmellose sodium | 3.5 |
| Calcium silicate | 5.0 |
| Aspartame | 1.5 |
| Colloidal silicon dioxide | 0.8 |
| Flavor | 0.5 |
| Polyethylene Glycol | 5.0 |
| Flavor | 0.2 |
| Sodium stearyl fumarate | 0.5 |
| Total | 100.0 |

All excipients except lubricant were blended in a blender to get a uniform mass. The mass was lubricated and compressed into tablets having following parameters:

| | |
|---|---|
| Hardness (N) | 10-20 |
| Friability (%) | 0.8-0.9 |
| In vitro disintegration time (sec) | 8-12 |
| Disintegration time in oral cavity (sec) | 30-40 |

Example 10

Wicking Test

The test is carried out to determine the rate of water uptake by the orally disintegrating tablets. Five circular tissue papers of about 10-cm diameter were placed in a petridish with a 10-cm diameter. Ten milliliters of water containing eosin, a water-soluble dye, was added to the petridish. A tablet (100 mg weight) was carefully placed on the surface of tissue paper. The time required for water to reach the upper surface of the tablets by capillary action was noted as the wicking time.

TABLE 4

Wicking time of various orally disintegrating tablets

| Formulation | Wicking Time (sec) |
| --- | --- |
| Example 1 | 15-20 |
| Example 8A | 35-40 |
| Example 8B | 18-20 |
| Example 9 | 20-22 |

Wicking time suggest that the spray dried composites exhibits lesser wicking time indicating rapid disintegration of these tablets. Between spray dried mannitol and the composite of the present invention, the composite gives much reduced wicking time.

Example 11

Orally Disintegrating Tablets of Drugs Having No Bitter Taste

TABLE 5

Compositions of orally disintegrating tablets

| Ingredients | mg/tablet | mg/tablet |
| --- | --- | --- |
| Clonazepam | 0.5 | — |
| Loratadine | — | 10.0 |
| Composite of example 2 | 55.0 | 45.0 |
| Starch | 22.5 | 18.0 |
| Croscarmellose sodium | 3.5 | 4.0 |
| Calcium silicate | 5.0 | 5.0 |
| Aspartame | 1.5 | 2.0 |
| Colloidal silicon dioxide | 0.8 | 0.8 |
| Flavor | 5.0 | 0.5 |
| Polyethylene Glycol | 0.2 | 4.2 |
| Sodium stearyl fumarate | 0.5 | 0.5 |
| Total | 90.0 | 90.0 |

The drug and the composite was mixed to get a premix. This premix was further mixed with other inactive ingredients, lubricated and compressed into tablets. All the tablets had good mouth feel and disintegrated in mouth within 60 sec.

Example 12

Orally Disintegrating Tablets of Tramadol Hydrochloride

TABLE 6

| Ingredients | mg/tablet |
| --- | --- |
| Taste masked tramadol equivalent to 50 mg tramadol hydrochloride | 108.0 |
| Composite of example 2 | 57.0 |
| Starch | 18.0 |
| Microcrystalline cellulose | 14.0 |
| Croscarmellose sodium | 4.5 |
| Sucralose | 0.25 |
| Aspartame | 2.0 |
| Colloidal silicon dioxide | 0.8 |
| Polyethylene Glycol | 4.0 |
| Flavor | 0.75 |
| Sodium stearyl fumarate | 0.5 |
| Total | 210 |

The drug and the composite was mixed to get a premix. This premix was further mixed with other inactive ingredients, lubricated and compressed into tablets.

All the tablets had good mouth feel and disintegrated in mouth within 60 sec.

Example 13

Orally Disintegrating Tablets of Taste Masked Donepezil

TABLE 7

| Ingredients | mg/tablet |
| --- | --- |
| Taste masked Donepezil equivalent to 10 mg Donepezil | 45.0 |
| Composite of example 2 | 60.0 |
| Starch | 18.0 |
| Microcrystalline cellulose | 10.0 |
| Croscarmellose sodium | 5.5 |
| Calcium silicate | 5.0 |
| Aspartame | 3.0 |
| Colloidal silicon dioxide | 0.8 |
| Sodium chloride | 3.5 |
| Flavor | 0.2 |
| Sodium stearyl fumarate | 0.5 |
| Total | 150.0 |

The drug and the composite was mixed to get a premix. This premix was further mixed with other inactive ingredients, lubricated and compressed into tablets having a lag time of less than 5 sec.

Example 14

Orally Disintegrating Tablets of High Dose Bitter Drug Paracetamol

TABLE 8

| Ingredients | mg/tablet |
|---|---|
| Taste masked paracetamol equivalent to 125 mg of paracetamol | 200 |
| Coprocessed composite of example 1 | 100 |
| Starch | 45 |
| Microcrystalline cellulose | 25 |
| Croscarmellose sodium | 7.0 |
| Calcium silicate | 10 |
| Aspartame | 4.0 |
| Colloidal silicon dioxide | 1.5 |
| Polyethylene Glycol | 5.5 |
| Flavor | 1.5 |
| Sodium chloride | 4.0 |
| Sodium stearyl fumarate | 1.5 |
| Total | 405 |

The drug and the composite were mixed to get a premix. This premix was further mixed with other inactive ingredients, lubricated and compressed into tablets. Tablets had desired wicking time of about 55 sec and a good mouth feel.

Example 15

Taste-masked Aripiprazole incorporated in Tablets along with spray-dried ODT Excipient prepared in Example 4.

TABLE 9

| Ingredients | (mg/tablet) |
|---|---|
| Taste-masked Aripiprazole Equivalet to 10.0 mg Aripiprazole | 30.0 |
| ODT Excipient (example 5) | 60.0 |
| Maize starch | 18.0 |
| Microcrystalline cellulose | 6.0 |
| PEG 4000 | 5.0 |
| POLYPLASDONE ® (crospovidone) | 7.5 |
| Aspartame | 1.0 |
| Peppermint | 0.5 |
| Blue FD & C | 0.2 |
| Magnesium stearate | 1.0 |
| AEROSIL ® 200 | 0.8 |
| Total | 130.0 |

Process:

The ingredients were sieved through 40# sieve along with taste-masked drug. The sieved mix was blended to homogenize, lubricated and compressed to obtain 130 mg tablets of the following properties:

| Hardness (N) | 15-22 |
|---|---|
| Friability (%) | 0.75 |
| In vitro disintegration time (sec) | 15 |
| Disintegration time in oral cavity (sec) | 30-40 |

Example 16

Taste-Masked Ropinirole Incorporated in Tablets Comprising Physical Mix of Spray-Dried Mannitol and Calcium Silicate in the Ratio 9:1

TABLE 10

| Ingredients | (mg/tablet) |
|---|---|
| Taste-masked ropinirole equivalent to 2.5 mg ropinirole | 10.0 |
| Coprocessed excipient of example 6 | 30.0 |
| Xylitol | 17.0 |
| Maize starch | 8.0 |
| Microcrystalline cellulose | 10.0 |
| PEG 4000 | 5.0 |
| POLYPLASDONE ® | 7.5 |
| Aspartame | 2.0 |
| Peppermint | 0.5 |
| Blue FD & C | 0.2 |
| Magnesium stearate | 1.0 |
| AEROSIL ® 200 | 8.8 |
| Total | 100.0 |

Process:

The ingredients were sieved through 40# sieve along with taste-masked drug. The sieved mix was blended to homogenize, lubricated and compressed to obtain 100 mg tablets of the following properties:

| Hardness (N) | 20-25 |
|---|---|
| Friability (%) | 0.5 |
| Wicking time (sec) | 30 |
| Disintegration time in oral cavity (sec) | 30 |

Example 17

Orally Disintegrating Tablets of Enteric Coated Esomeprazole

TABLE 11

| Ingredients | (mg/tablet) |
|---|---|
| Enteric-coated esomeprazole pellets equivalent to 20 mg esomeprazole | 35.0 |
| ODT Excipient (example 7) | 140.0 |
| Silicified Microcrystalline cellulose | 60.0 |
| PEG 4000 | 5.0 |
| POLYPLASDONE ® | 7.5 |
| Aspartame | 0.45 |
| Peppermint | 0.25 |
| Magnesium stearate | 1.0 |
| AEROSIL ® 200 | 0.8 |
| Total | 250.0 |

Process:

The ingredients were sieved through 40# sieve along and was blended to homogenize, lubricated and compressed to obtain 250 mg tablets of the following properties:

| Hardness (N) | 40 |
|---|---|
| Friability (%) | 0.6 |

-continued

| | |
|---|---|
| Wicking time (sec) | 45 |
| Disintegration time in oral cavity (sec) | 50 |

Example 18

Orally Disintegrating Tablets of Memantine

TABLE 12

| Ingredients | (mg/tablet) |
|---|---|
| Taste-masked memantine equivalent to 20.0 mg memantine | 40.0 |
| ODT Excipient (example 7) | 115.0 |
| Pregelatinised starch | 18.0 |
| Powdered cellulose | 24.0 |
| Sodium chloride | 2.0 |
| POLYPLASDONE ® | 7.5 |
| Sodium saccharine | 1.0 |
| Orange flavor | 0.5 |
| Blue FD & C | 0.2 |
| Magnesium stearate | 1.0 |
| AEROSIL ® 200 | 0.8 |
| Total | 210.0 |

Process:

The ingredients were sieved through 40# sieve along with taste-masked drug. The sieved mix was blended to homogenize, lubricated and compressed to obtain 210 mg tablets of the following properties:

| | |
|---|---|
| Hardness (N) | 45 |
| Friability (%) | 0.3 |
| Wicking time (sec) | 48 |
| Disintegration time in oral cavity (sec) | 40-50 |

Example 19

Figure 2:
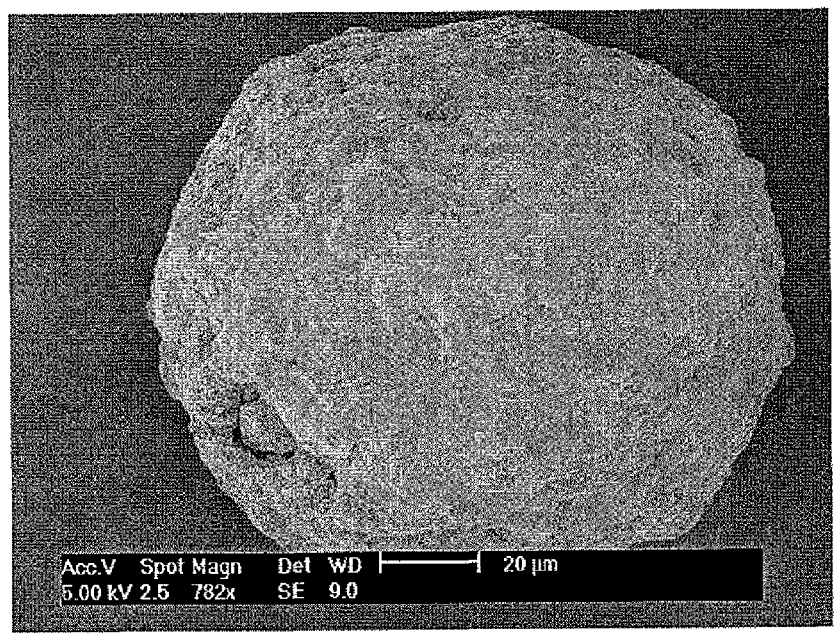
FIG. 2 is an illustration of a SEM micrograph of a single particle of the composite excipient of the present invention according to Example 19.

Preparation of Composite Excipients of Mannitol 75% and Calcium Silicate 25% According to Present Invention The composite excipients consisting of mannitol at 75% and calcium silicate at 25% were produced by a spray dry granulation process. The apparatus used for the production of the excipient was a Co-current atomizer disc type with the disc RPM between 12000 and 25000 and the inlet temperatures of 180-250° C. Mannitol was dissolved in deionized water in a mixing chamber to give a concentration of 22.5%. Calcium silicate was then added to the solution to achieve the total solid content of 30% in the slurry. The slurry was mixed to form uniform mixture at 40-60° C. for 2 hours using an agitator to keep solid suspended in the solution to form uniform slurry. The slurry mixture was then spray dried through a rotary nozzle at a motor frequency of 33 Hz in the presence of hot air at an outlet temperature of 106-109° C. This constitutes the particle formation step. The fines were removed in a cyclone and the final product was collected to give the new composite excipient. SEM micrographs of the composite of Example 19 are shown in FIG. 1. Unless otherwise noted, all SEM micrographs herein were recorded using a FEI XL30 ESEM (environmental scanning electron microscope), voltage 5 kV, spot size 3, SE detector. The samples were sputtered with Iridium before SEM analysis (sputtering time 40 sec.)

The compressibility, aerated bulk density and tapped bulk density of the composite were measured using a Powder Tester (THERMONIK®). For measuring the aerated bulk density and tapped bulk density a 50 cc measuring cylinder was employed. The standard tapping counts for measuring the tapped bulk density were 50 which was repeated until the difference in volume between two consecutive 50 taps is less than 1 ml. Particle size distribution was determined by taking sieves of #60, #100 and #200. A fixed amount of powder (.about.100 g) was introduced at the top of #60 sieve and the sieve shaker was started for a period of 10 min.

The "loss on drying" (LOD) value was determined using a Mettler Toledo Infrared Dryer HB43. The set temperature was 105° C. and the instrument is automatically stopped when the difference in the weight recorded is less than 1 mg/50 sec.

TABLE 13

| Powder Characteristics | Value |
|---|---|
| 1. Compressibility (%) | 10.9 |
| 2. Angle of repose | 21.3 |
| 3. Aerated bulk density (g/cc) | 0.64 |
| 4. Tapped bulk density (g/cc) | 0.74 |
| 5. LOD (%) | 3.88 |
| 6. Particle size Distribution | |

| Sieve Number | Cumulative % retained |
|---|---|
| 60# | 2.55 |
| 100# | 48.13 |
| 200# | 87.38 |

The composite excipient produced according to this example exhibited good compressibility, particle size distribution and flow characteristics desired for its performance as a tablet excipient.

Example 20

Preparation of Granules of Mannitol 90% and Calcium Silicate 10% According to Present Invention The composite excipients consisting of mannitol at 90% and calcium silicate at 10% were produced by a spray drying process. The apparatus used for the production of the composite excipients was a Co-current atomizer disc type with the disc RPM between 12000 and 25000 and the inlet temperatures of 180-250° C. Mannitol was dissolved in deionized water in a mixing chamber to give a concentration of 27%. Calcium silicate was then added to the solution to achieve the total solid content of 30% in the slurry. The slurry was mixed to form a uniform mixture at 40-60° C. for 2 hours using an agitator to keep solid suspended in the solution to form a uniform slurry. The slurry mixture was then spray dried through a rotary nozzle at a motor frequency of 33 Hz in the presence of hot air at an outlet temperature of 106-109° C. This constitutes the granule formation step. The fines were removed in a cyclone and the final product was collected to give the new improved excipient.

TABLE 14

| Powder Characteristics | Value |
|---|---|
| 1. Compressibility | 20.1 |
| 2. Aerated bulk density | 0.59 |
| 3. Tapped bulk density | 0.72 |
| 4. LOD | 2.48 |

TABLE 14-continued

| | |
|---|---|
| 5. Angle of Repose | 19.5 |
| 6. Particle size Distribution | |

| Sieve Number | Cumulative % retained |
|---|---|
| 60# | 1.07 |
| 100# | 25.92 |
| 200# | 99.9 |

The composite produced according to this example with different ratio of mannitol and calcium silicate also exhibited good compressibility, particle size distribution and flow characteristics desired for its performance as a tablet excipient.

Example 21

Preparation of Composite Excipient of Mannitol 85% and Calcium Silicate 15% According to Present Invention The composite consisting of mannitol at 85% and calcium silicate at 15% produced by a spray drying process. The apparatus used for the production of the excipient was a co-current atomizer disc type with the disc RPM between 12000 and 25000 and the inlet temperatures of 180-250° C. Mannitol was dissolved in deionized water in a mixing chamber to give a concentration of 25.5%. Calcium silicate was then added to the solution to achieve the total solid content of 30% in the slurry. The slurry was mixed to form a uniform mixture at 40-60° C. for 2 hours using an agitator to keep solid suspended in the solution to form uniform slurry. The slurry mixture was then spray dried through a rotary nozzle at a motor frequency of 33 Hz in the presence of hot air at an outlet temperature of 106-109° C. This constitutes the granule formation step. The fines were removed in a cyclone and the final product was collected to give the new improved excipient.

TABLE 15

| Powder Characteristics | Value |
|---|---|
| 1. Compressibility | 20.0 |
| 2. Aerated bulk density | 0.58 |
| 3. Tapped bulk density | 0.72 |
| 4. LOD | 1.69 |
| 5. Angle of Repose | 22.35 |
| 6. Particle size Distribution | |

| Sieve Number | Cumulative % retained |
|---|---|
| 60# | 5.8 |
| 100# | 15.4 |
| 200# | 99.4 |

The composite produced according to this example with different ratio of mannitol and calcium silicate exhibited physical parameters suited for direct compression of the tablets.

Example 22

Preparation of Composite Excipient of Mannitol 85%, Polyethylene Glycol 5% and Calcium Silicate 10% According to Present Invention The composite consisting of mannitol at 85%, polyethylene glycol 5% and calcium silicate at 10% was produced by a wet spray drying process. The apparatus used for the production of the composite was a spray dryer attached with nozzle for spraying the slurry and the inlet temperatures of 180-250° C. Mannitol was dissolved in deionized water in a mixing chamber to give a concentration of 25.5%, further polyethylene glycol was added to it to give a concentration of 1.5%. Calcium silicate was then added to the solution to achieve the total solid content of 30% in the slurry. An agitator was employed to keep solid suspended in the solution to form uniform slurry. The slurry mixture was then spray dried through a nozzle having a diameter of 1-5 mm at an atomizing pressure of 0.2 Kgf/cm$^2$ in the presence of hot air at an outlet temperature of 106-125° C. This constitutes the granule formation step.

TABLE 16

| Powder Characteristics | Value |
|---|---|
| 1. Compressibility | 23.0 |
| 2. Aerated bulk density | 0.53 |
| 3. Tapped bulk density | 0.69 |
| 4. LOD | 0.50 |

The composite produced with addition of polyethylene glycol according to this example produced particles having desired properties.

Example 23

Preparation of Composite Excipient of Mannitol 70% and Calcium Silicate 30%

40 g of mannitol was dissolved in water at room temperature. In this solution 30 g of calcium silicate was added and stirred to get a uniform mass. 30 g mannitol was used as a bed in the form of powder. This powder was fluidized using a hot air stream. The mass of mannitol and calcium silicate was atomized in the fluidized bed processor at inlet temperature of 60-70° C. using 1.0 mm nozzle at an atomization pressure of 1-2 Kg/cm$^2$. The granules obtained were free flowing with bulk density in the range of 0.7-0.8 g/cc. LOD was found to be in the range 0.35 to 0.40

Example 24

Physical Mix of Mannitol and Calcium Silicate

Mannitol and calcium silicate were mixed in the ratio of 75:25 in a drum blender for 30 min. Physical properties of the blend is as follows:

TABLE 17

| Powder Characteristics | Value |
|---|---|
| 1. Compressibility | 32.58 |
| 2. Aerated bulk density | 0.6 |
| 3. Tapped bulk density | 0.89 |
| 4. LOD | 0.70 |
| 5. Angle of repose | Could not be determined as material did not flow through the funnel |

Figure 5:
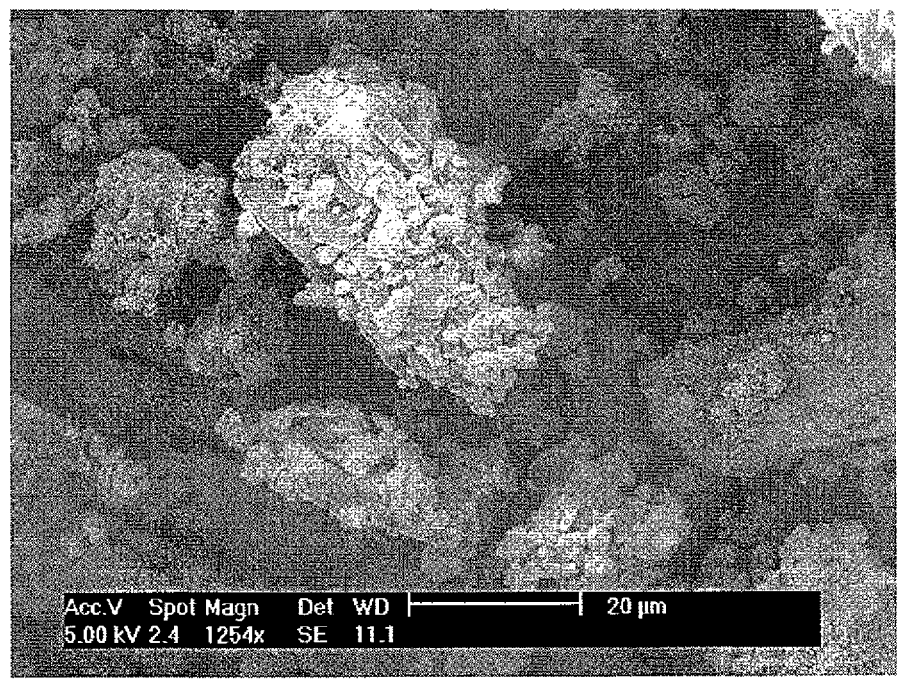
FIG. 5 is an illustration of a SEM micrograph of physically mixed calcium silicate and mannitol according to Example 24.

FIG. 5 is a SEM micrograph of the physically mixed excipient prepared according to Example 24. SEM micrographs of calcium silicate and mannitol can be found at FIGS. 3 and 4 respectively.

Example 25

Tablet Formulation Using Excipient of Example 19 or 20 and the Material Obtained by Physical Mixing as Per Example 24 Comparison Using Wicking Test Comparative evaluation of composites prepared by homogeneous granules and physical mixing was conducted by making tablets as per the formula given below (ODT excipient means percent of calcium silicate: mannitol mix).

TABLE 18

ODT tablet composition

| Ingredient | % w/w |
| --- | --- |
| ODT Excipient of example 1 or 2, 6 | 60.0 |
| Maize starch | 18.2 |
| Microcrystalline cellulose | 11.0 |
| POLYPLASDONE ® XL10 | 7.5 |
| Aspartame | 1.0 |
| Peppermint flavor | 0.5 |
| AEROSIL ® 200 | 0.8 |
| Magnesium stearate | 1.0 |
| Total (Tablet weight) | 100.0 mg |
| Tablet size | 7.0 mm |
| Tablet hardness | 20-40 N |
| Friability | <1% |

The following data gives average wicking time data of tablets prepared using composite prepared using spray drying process.

Comparative Evaluation of Physical Mixing and Spray Dried Product

TABLE 19

| Excipient | Process | Average wicking time (sec) | Average lag time (sec) | Average mouth dissolution time (sec) |
| --- | --- | --- | --- | --- |
| Example 19 | Spray drying | 13 | 3 | 18 |
| Example 20 | Spray drying | 17 | 4 | 23 |
| Example 24 | Physical mixing | 29 | 5 | 45 |

The data shown indicate that the wicking time and lag time of the tablets prepared using composite excipient is much better than physical mixing. In addition, there is a significant difference in the mouth dissolution time which is much higher in case of tablets prepared using physical mixing process also a slight core was left in the mouth which took longer time to disintegrate. Tablets moreover gave a chalky taste which is not acceptable for a good orally disintegrating tablet formulation. The tabletting mixture produced with physical mixture of calcium silicate along with mannitol also produced mixture with poor flow which made difficult to make good tablets. This also made it difficult to increase the amount of calcium silicate in the formulation. During continued processing of tablets (compression), blackening of the blend on the turret was observed which resulted in unacceptable black spots on the surface of the tablet.

Example 26

Comparison of wicking time and in-vivo disintegration time of tablets prepared using Composite of Example 19, excipient from different commercial sources (F-melt, Pharmaburst).

Figure 6:
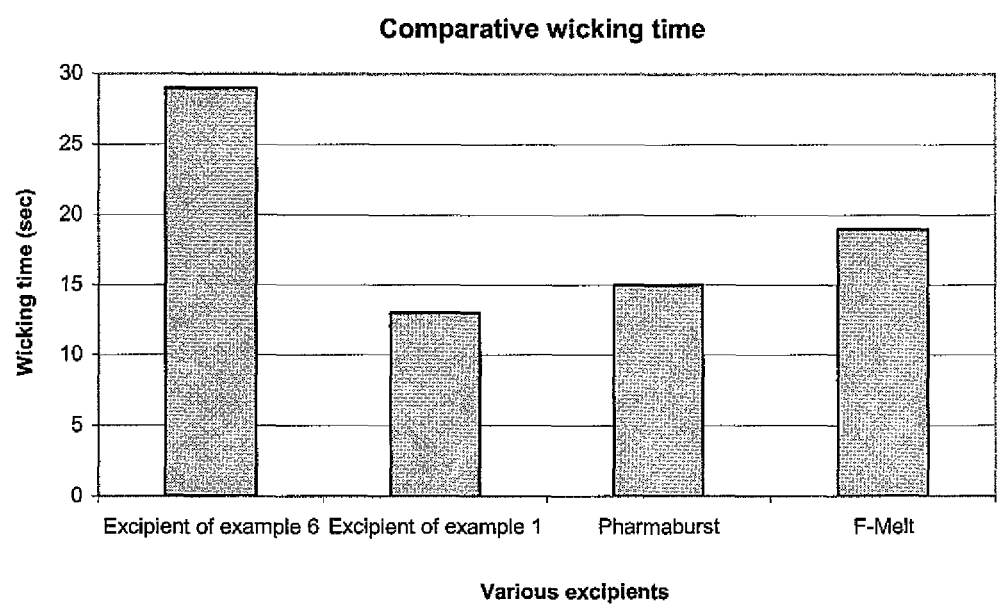
FIG. 6 is a graph depicting the data of the wicking test on various ODT excipients according to Example 26.

In the composition of Example 25 composite of Example 19 was replaced with F-MELT® (commercially available spray-dried powder ODT excipient from Fuji Chemical) in one trial and with PHARMABURST® (commercial available co-processed excipient from SPI Pharma) in another trial and the wicking time was determined. The wicking test is carried out to determine the rate of water uptake by the orally disintegrating tablets. Five circular tissue papers of about 10-cm diameter were placed in a petridish with a 10-cm diameter. Ten milliliters of water containing eosin, a water-soluble dye, was added to the petridish. A tablet (100 mg weight) was carefully placed on the surface of tissue paper, The time required for water to reach the upper surface of the tablets by capillary action was noted as the wicking time. FIG. 6 is a graph depicting the data of the wicking test on various ODT excipients.

Example 27

Tablet formulation using composite of Example 19 and a combination of spray dried mannitol and calcium silicate:

TABLE 20

Compositions of orally disintegrating tablets using composites and spray dried mannitol

| Ingredients | A mg/tablet | B mg/tablet |
| --- | --- | --- |
| Spray dried mannitol | 45.0 | — |
| Composite excipient of example 19 | — | 50.0 |
| Starch | 23.0 | 23.0 |
| Microcrystalline cellulose | 10.0 | 10.0 |
| Croscarmellose sodium | 3.5 | 3.5 |
| Calcium silicate | 10.0 | 5.0 |
| Aspartame | 1.5 | 1.5 |
| Colloidal silicon dioxide | 0.8 | 0.8 |
| Flavor | 0.5 | 0.5 |
| Polyethylene Glycol | 5.0 | 5.0 |
| Flavor | 0.2 | 0.2 |
| Sodium stearyl fumarate | 0.5 | 0.5 |
| Total | 100.0 | 100.0 |

All excipients except lubricant were blended in a blender to get a uniform mass. The mass was lubricated and compressed into tablets having following parameters:

TABLE 21

| | A | B |
| --- | --- | --- |
| Hardness (N) | 10-20 | 10-20 |
| Friability (%) | 0.85 | 1.0 |
| In vitro Disintegration time (sec) | 15-20 | 5-10 |
| Disintegration time in oral cavity (sec) | 40-50 | 25-40 |

Robust tablets were obtained with low friability and desired disintegration time.

Example 28

Orally Disintegrating Tablets of Drugs Having No Bitter Taste

TABLE 22

Compositions of orally disintegrating tablets

| Ingredients | mg/tablet | mg/tablet |
|---|---|---|
| Clonazepam | 0.5 | — |
| Loratadine | — | 10.0 |
| Homogeneous granules of Example 19 | 55.0 | 45.0 |
| Starch | 22.5 | 18.0 |
| Croscarmellose sodium | 3.5 | 4.0 |
| Calcium silicate | 5.0 | 5.0 |
| Aspartame | 1.5 | 2.0 |
| Colloidal silicon dioxide | 0.8 | 0.8 |
| Flavor | 5.0 | 0.5 |
| Polyethylene Glycol | 0.2 | 4.2 |
| Sodium stearyl fumarate | 0.5 | 0.5 |
| Total | 90.0 | 90.0 |

The drug and the composite was mixed to get a premix, This premix was further mixed with other inactive ingredients, lubricated and compressed into tablets, All the tablets had good mouth feel and disintegrated in mouth within 60 sec.

Example 29

Orally Disintegrating Tablets of Tramadol Hydrochloride

TABLE 23

Compositions of orally disintegrating tablets

| Ingredients | mg/tablet |
|---|---|
| Taste masked tramadol equivalent to 50 mg tramadol hydrochloride | 108.0 |
| Composite excipient of example 19 | 57.0 |
| Starch | 18.0 |
| Microcrystalline cellulose | 14.0 |
| Croscarmellose sodium | 4.5 |
| Sucralose | 0.25 |
| Aspartame | 2.0 |
| Colloidal silicon dioxide | 0.8 |
| Polyethylene Glycol | 4.0 |
| Flavor | 0.75 |
| Sodium stearyl fumarate | 0.5 |
| Total | 210 |

The drug and the composite were mixed to get a premix. This premix was further mixed with other inactive ingredients, lubricated and compressed into tablets.

All the tablets had good mouth feel and disintegrated in mouth within 60 sec.

Example 30

Orally Disintegrating Tablets of Taste Masked Donepezil

TABLE 24

Compositions of orally disintegrating tablets

| Ingredients | mg/tablet |
|---|---|
| Taste masked Donepezil equivalent to 10 mg Donepezil | 45.0 |
| Composite excipient of example 19 | 60.0 |
| Starch | 18.0 |
| Microcrystalline cellulose | 10.0 |
| Croscarmellose sodium | 5.5 |
| Calcium silicate | 5.0 |
| Aspartame | 3.0 |
| Colloidal silicon dioxide | 0.8 |
| Sodium chloride | 3.5 |
| Flavor | 0.2 |
| Sodium stearyl fumarate | 0.5 |
| Total | 150.0 |

The drug and the composite were mixed to get a premix. This premix was further mixed with other inactive ingredients, lubricated and compressed into tablets having a lag time of less than 5 sec.

Example 31

Orally Disintegrating Tablets of High Dose Bitter Drug Paracetamol

TABLE 25

Compositions of orally disintegrating tablets

| Ingredients | mg/tablet |
|---|---|
| Taste masked paracetamol equivalent to 125 mg of paracetamol | 200 |
| Composite excipient of example 19 | 100 |
| Starch | 45 |
| Microcrystalline cellulose | 25 |
| Croscarmellose sodium | 7.0 |
| Calcium silicate | 10 |
| Aspartame | 4.0 |
| Colloidal silicon dioxide | 1.5 |
| Polyethylene Glycol | 5.5 |
| Flavor | 1.5 |
| Sodium chloride | 4.0 |
| Sodium stearyl fumarate | 1.5 |
| Total | 405 |

The drug and the composite were mixed to get a premix. This premix was further mixed with other inactive ingredients, lubricated and compressed into tablets. Tablets had desired wicking time of about 55 sec and a good mouth feel.

Example 32

Taste-Masked Aripiprazole Incorporated in Tablets Along with Spray-Dried ODT Excipient Prepared in Example 23

TABLE 26

| Ingredients | (mg/tablet) |
|---|---|
| Taste-masked Aripiprazole | 30.0 |
| Equivalent to 10.0 mg Aripiprazole | |
| Composite excipient of example 2 | 60.0 |
| Maize starch | 18.0 |
| Microcrystalline cellulose | 6.0 |
| PEG 4000 | 5.0 |
| POLYPLASDONE ® | 7.5 |
| Aspartame | 1.0 |
| Peppermint | 0.5 |
| Blue FD & C | 0.2 |
| Magnesium stearate | 1.0 |
| AEROSIL ® 200 | 0.8 |
| Total | 130.0 |

Process: The ingredients were sieved through 40# sieve along with taste-masked drug. The sieved mix was blended to homogenize, lubricated and compressed to obtain 130 mg tablets of the following properties:

| | |
|---|---|
| Hardness (N) | 15-22 |
| Friability (%) | 0.75 |
| Disintegration time (sec) | 15 |
| Disintegration time in oral cavity (sec) | 30-40 |

Tablets had desired disintegration time of about 30-40 sec in oral cavity and a good mouth feel. The lag time was about 4 seconds.

Example 33

Taste-Masked Ropinirole Incorporated in Tablets Comprising Physical Mix of Spray-Dried Mannitol and Calcium Silicate in the Ratio 9:1

TABLE 27

| Ingredients | (mg/tablet) |
|---|---|
| Taste-masked ropinirole | 10.0 |
| equivalent to 2.5 mg ropinirole | |
| Composite excipient of example 3 | 30.0 |
| Xylitol | 17.0 |
| Maize starch | 8.0 |
| Microcrystalline cellulose | 10.0 |
| PEG 4000 | 5.0 |
| POLYPLASDONE ® | 7.5 |
| Aspartame | 2.0 |
| Peppermint | 0.5 |
| Blue FD & C | 0.2 |
| Magnesium stearate | 1.0 |
| AEROSIL ® 200 | 8.8 |
| Total | 100.0 |

Process: The ingredients were sieved through 40# sieve along with taste-masked drug. The sieved mix was blended to homogenize, lubricated and compressed to obtain 100 mg tablets of the following properties:

| | |
|---|---|
| Hardness (N) | 20-25 |
| Friability (%) | 0.5 |
| Wicking time (sec) | 30 |
| Disintegration time in oral cavity (sec) | 30 |

Example 34

Orally Disintegrating Tablets of Enteric Coated Esomeprazole

TABLE 28

| Ingredients | (mg/tablet) |
|---|---|
| Enteric-coated esomeprazole pellets | 35.0 |
| equivalent to 20 mg esomeprazole | |
| Composite excipient of example 4 | 140.0 |
| Silicified Microcrystalline cellulose | 60.0 |
| PEG 4000 | 5.0 |
| POLYPLASDONE ® | 7.5 |
| Aspartame | 0.45 |
| Peppermint | 0.25 |
| Magnesium stearate | 1.0 |
| AEROSIL ® 200 | 0.8 |
| Total | 250.0 |

Process: The ingredients were sieved through 40# sieve along and was blended to homogenize, lubricated and compressed to obtain 250 mg tablets of the following properties:

| | |
|---|---|
| Hardness (N) | 40 |
| Friability (%) | 0.6 |
| Wicking time (sec) | 45 |
| Disintegration time in oral cavity (sec) | 50 |

Example 35

Orally Disintegrating Tablets of Memantine

TABLE 29

| Ingredients | (mg/tablet) |
|---|---|
| Taste-masked memantine | 40.0 |
| equivalent to 20.0 mg memantine | |
| Composite excipient of example 4 | 115.0 |
| Pregelatinised starch | 18.0 |
| Powdered cellulose | 24.0 |
| Sodium chloride | 2.0 |
| POLYPLASDONE ® | 7.5 |
| Sodium saccharine | 1.0 |
| Orange flavor | 0.5 |
| Blue FD & C | 0.2 |
| Magnesium stearate | 1.0 |
| AEROSIL ® 200 | 0.8 |
| Total | 210.0 |

Process: The ingredients were sieved through 40# sieve along with taste-masked drug. The sieved mix was blended to homogenize, lubricated and compressed to obtain 210 mg tablets of the following properties:

| | |
|---|---|
| Hardness (N) | 45 |
| Friability (%) | 0.3 |
| Wicking time (sec) | 48 |
| Disintegration time in oral cavity (sec) | 40-50 |

The invention claimed is:

1. A composite excipient consisting of calcium silicate particles substantially completely covered by and in contact with mannitol.

2. The composite of claim 1 wherein the calcium silicate comprises about 5% to about 50% of the composite by weight, and the mannitol comprises about 50% to about 95% of the composite by weight.

3. The composite excipient of claim 1 wherein the calcium silicate comprises about 25% of the composite by weight, and the mannitol comprises about 75% of the composite by weight.

4. The composite excipient of claim 1 wherein the composite excipient has an average particle size of at least about 50 micrometers.

5. A method of making the composite excipient, the method comprising:
adding mannitol to water;
heating the solution to a temperature at which mannitol is substantially dissolved to form a solution;
adding calcium silicate with stirring to the solution to form a slurry;
drying the slurry in a heated air stream to form calcium silicate that is substantially completely covered by and in contact with mannitol.

6. An orally disintegrating tablet comprising:
a. at least one pharmaceutically active ingredient or nutraceutical; and
b. a composite excipient consisting of calcium silicate particles substantially completely covered by and in contact with mannitol, whereby the calcium silicate is prevented from reacting with the active pharmaceutical ingredient.

7. The orally disintegrating tablet of claim 6 further including a salivating agent.

8. The orally disintegrating tablet of claim 6 wherein the calcium silicate comprises about 5% to about 50% of the composite excipient by weight, and the mannitol comprises about 50% to about 95% of the composite excipient by weight.

9. The orally disintegrating tablet of claim 6 wherein the composite excipient has an average particle size of at least about 50 micrometers.

* * * * *

UNITED STATES PATENT AND TRADEMARK OFFICE
CERTIFICATE OF CORRECTION

| | | |
|---|---|---|
| PATENT NO. | : 8,545,890 B2 | Page 1 of 1 |
| APPLICATION NO. | : 12/270905 | |
| DATED | : October 1, 2013 | |
| INVENTOR(S) | : Pilgaonkar et al. | |

It is certified that error appears in the above-identified patent and that said Letters Patent is hereby corrected as shown below:

In the Specification:

Column 23, line 33

Now reads:    "was mixed to get a premix,";

Should read:    -- was mixed to get a premix." --.

Column 23, line 35

Now reads:    "and compressed into tablets, All";

Should read:    -- and compressed into tablets. All --.

In the Claims:

Column 27, line 24

Now reads:    "making the composite excipient, the";

Should read:    -- making the composite excipient of Claim 1, the --.

Signed and Sealed this
Eleventh Day of March, 2014

Michelle K. Lee
*Deputy Director of the United States Patent and Trademark Office*